US012440668B2

(12) United States Patent
Lee et al.

(10) Patent No.: US 12,440,668 B2
(45) Date of Patent: Oct. 14, 2025

(54) COCHLEAR IMPLANTS HAVING MRI-COMPATIBLE MAGNET APPARATUS AND ASSOCIATED SYSTEMS AND METHODS

(71) Applicant: ADVANCED BIONICS AG, Staefa (CH)

(72) Inventors: Sung Jin Lee, Valencia, CA (US); James George Elcoate Smith, Santa Clarita, CA (US)

(73) Assignee: Advanced Bionics AG, Staefa (CH)

(*) Notice: Subject to any disclaimer, the term of this patent is extended or adjusted under 35 U.S.C. 154(b) by 803 days.

(21) Appl. No.: 17/499,813

(22) Filed: Oct. 12, 2021

(65) Prior Publication Data

US 2023/0115968 A1 Apr. 13, 2023

(51) Int. Cl.
*A61N 1/00* (2006.01)
*A61N 1/05* (2006.01)
*A61N 1/372* (2006.01)

(52) U.S. Cl.
CPC ....... *A61N 1/0541* (2013.01); *A61N 1/37223* (2013.01)

(58) Field of Classification Search
None
See application file for complete search history.

(56) References Cited

U.S. PATENT DOCUMENTS 4,214,366 A 7/1980 Laban
4,352,960 A 10/1982 Dormer et al.
4,595,390 A 6/1986 Hakim et al.
4,606,329 A 8/1986 Hough
4,612,915 A 9/1986 Hough et al.
(Continued)

FOREIGN PATENT DOCUMENTS

CN 212542072 U 2/2021
DE 202006017662 U1 9/2007
(Continued)

OTHER PUBLICATIONS

N55: King of the permanent NDFEB Magnet. Magnets by HSMAG. (Apr. 15, 2020). https://www.hsmagnets.com/blog/n55-king-of-the-permanent-ndfeb-magnet/ (Year: 2020).*
(Continued)

*Primary Examiner* — Niketa Patel
*Assistant Examiner* — Anant A Gupta
(74) *Attorney, Agent, or Firm* — Henricks Slavin LLP

(57) ABSTRACT

A system including a cochlear implant with a cochlear lead including a plurality of electrodes, an antenna, a stimulation processor operably connected to the antenna and to the cochlear lead, and a magnet apparatus, adjacent to the antenna, including a case defining a central axis, a frame within the case and rotatable relative to the case about the central axis of the case, and only two elongate diametrically magnetized magnets that are located in the frame, that are separated from one another by a fixed non-zero distance, that each define a longitudinal axis and a N-S direction, and that are rotatable about the longitudinal axis relative to the frame, and an external device including an axially magnetized disk-shaped positioning magnet and an antenna adjacent to the axially magnetized disk-shaped positioning magnet.

15 Claims, 6 Drawing Sheets

(56) References Cited

U.S. PATENT DOCUMENTS 4,618,949 A 10/1986 Lister
RE32,947 E 6/1989 Dormer et al.
5,290,281 A 3/1994 Tschakaloff
5,755,762 A 5/1998 Bush
5,824,022 A 10/1998 Zilberman et al.
5,945,762 A 8/1999 Chen et al.
6,032,677 A 3/2000 Blechman et al.
6,178,353 B1 1/2001 Griffith et al.
6,190,305 B1 2/2001 Ball et al.
6,217,508 B1 4/2001 Ball et al.
6,227,820 B1 5/2001 Jarvik
6,292,678 B1 9/2001 Hall et al.
6,348,070 B1 2/2002 Teissl et al.
6,358,281 B1 3/2002 Berrang et al.
6,461,288 B1 10/2002 Holcomb
6,599,321 B2 7/2003 Hyde, Jr.
6,838,963 B2 1/2005 Zimmerling
7,091,806 B2 8/2006 Zimmerling et al.
7,190,247 B2 3/2007 Zimmerling
7,266,208 B2 9/2007 Charvin et al.
7,566,296 B2 7/2009 Zimmerling et al.
7,609,061 B2 10/2009 Hochmair
7,642,887 B2 1/2010 Zimmerling
7,680,525 B1 3/2010 Damadian
7,729,774 B1 6/2010 Lynch et al.
7,774,069 B2 8/2010 Olson et al.
7,856,986 B2 12/2010 Darley
7,881,800 B2 2/2011 Daly et al.
7,976,453 B2 7/2011 Zimmerling et al.
8,013,699 B2 9/2011 Zimmerling
8,027,735 B1 9/2011 Tziviskos et al.
8,118,725 B2 2/2012 Zimmerling et al.
8,255,058 B2 8/2012 Gibson et al.
8,340,774 B2 12/2012 Hochmair et al.
8,634,909 B2 1/2014 Zimmerling et al.
8,733,494 B1 5/2014 Leigh
8,734,475 B2 5/2014 Ekvall et al.
8,744,106 B2 6/2014 Ball
8,758,394 B2 6/2014 Zimmerling et al.
8,787,608 B2 7/2014 Van Himbeeck et al.
8,790,409 B2 7/2014 Van den Heuvel et al.
8,825,171 B1 9/2014 Thenuwara et al.
8,891,795 B2 11/2014 Andersson
8,897,475 B2 11/2014 Ball et al.
RE45,701 E 9/2015 Zimmerling et al.
9,126,010 B2 9/2015 Shah et al.
9,162,054 B2 10/2015 Dalton
9,227,064 B2 1/2016 Duftner
9,295,425 B2 3/2016 Ball
9,314,625 B2 4/2016 Kasic, II et al.
9,352,149 B2 5/2016 Thenuwara et al.
RE46,057 E 7/2016 Zimmerling et al.
9,392,382 B1 7/2016 Nagl et al.
9,420,388 B2 8/2016 Ball
9,549,267 B2 1/2017 Nagl et al.
9,615,181 B2 4/2017 Nagl et al.
9,656,065 B2 5/2017 Tourrel et al.
9,919,154 B2* 3/2018 Lee ........................... H01F 7/02
9,931,501 B2 4/2018 Smyth
10,300,276 B2 5/2019 Lee et al.
10,463,849 B2 11/2019 Lee et al.
10,532,209 B2 1/2020 Lee et al.
10,646,712 B2 5/2020 Smith et al.
10,646,718 B2 5/2020 Smith et al.
10,806,936 B2 10/2020 Crawford et al.
10,821,279 B2 11/2020 Lee et al.
11,097,095 B2 8/2021 Smith et al.
11,287,495 B2 3/2022 Smith et al.
11,304,015 B2 4/2022 Haagerup
11,364,384 B2 6/2022 Smith et al.
11,471,679 B2 10/2022 Smith et al.
11,476,025 B2 10/2022 Lee et al.
11,638,823 B2 5/2023 Brehm et al.
11,752,338 B2 9/2023 Smith et al.
11,779,754 B2 10/2023 Smith et al.
11,986,656 B2 5/2024 Lee et al.
2004/0012470 A1 1/2004 Zimmerling et al.
2004/0059423 A1 3/2004 Barnes et al.
2004/0063072 A1 4/2004 Honkura et al.
2004/0210103 A1 10/2004 Westerkull
2004/0260362 A1 12/2004 Darley
2005/0001703 A1 1/2005 Zimmerling
2005/0004629 A1 1/2005 Gibson et al.
2005/0062567 A1 3/2005 Zimmerling et al.
2006/0015155 A1 1/2006 Charvin et al.
2006/0116743 A1 6/2006 Gibson et al.
2006/0244560 A1 11/2006 Zimmerling et al.
2007/0053536 A1 3/2007 Westerkull
2007/0126540 A1 6/2007 Zimmerling
2008/0097496 A1 4/2008 Chang et al.
2008/0103350 A1 5/2008 Farone
2008/0192968 A1 8/2008 Ho et al.
2008/0195178 A1 8/2008 Kuzma
2009/0048580 A1 2/2009 Gibson
2009/0099403 A1 4/2009 Zimmerling et al.
2009/0134721 A1 5/2009 Zimmerling
2009/0248155 A1 10/2009 Parker
2009/0287278 A1 11/2009 Charvin
2010/0004716 A1 1/2010 Zimmerling et al.
2010/0036458 A1 2/2010 Duftner et al.
2010/0046778 A1 2/2010 Crawford et al.
2010/0046779 A1 2/2010 Crawford et al.
2011/0009925 A1 1/2011 Leigh et al.
2011/0022120 A1 1/2011 Ball et al.
2011/0068885 A1 3/2011 Fullerton et al.
2011/0218605 A1 9/2011 Cryer
2011/0224756 A1 9/2011 Zimmerling et al.
2011/0255731 A1 10/2011 Ball
2011/0264172 A1 10/2011 Zimmerling et al.
2012/0296155 A1 11/2012 Ball
2013/0079749 A1 3/2013 Overstreet et al.
2013/0150657 A1 6/2013 Leigh et al.
2013/0184804 A1 7/2013 Dalton
2013/0281764 A1 10/2013 Bjorn et al.
2013/0343588 A1 12/2013 Karunasiri
2014/0005750 A1 1/2014 Garnham et al.
2014/0012069 A1 1/2014 Ball
2014/0012070 A1 1/2014 Nagl et al.
2014/0012071 A1 1/2014 Nagl et al.
2014/0012349 A1 1/2014 Zimmerling
2014/0121449 A1 5/2014 Kasic et al.
2014/0121586 A1 5/2014 Bertrand et al.
2014/0163692 A1 6/2014 Van den Heuvel et al.
2014/0336447 A1 11/2014 Bjorn et al.
2014/0343626 A1 11/2014 Thenuwara et al.
2015/0025613 A1 1/2015 Nyberg, II et al.
2015/0073205 A1 3/2015 Ball et al.
2015/0087892 A1 3/2015 Tourrel et al.
2015/0094521 A1 4/2015 Neuman et al.
2015/0100109 A1 4/2015 Feldman et al.
2015/0112407 A1 4/2015 Hartley et al.
2015/0265842 A1 9/2015 Ridler
2015/0320523 A1 11/2015 Way et al.
2015/0367126 A1 12/2015 Smyth
2015/0374989 A1 12/2015 Hazard et al.
2015/0382114 A1 12/2015 Andersson et al.
2016/0008596 A1 1/2016 Gibson et al.
2016/0023006 A1 1/2016 Ridler et al.
2016/0037273 A1 2/2016 Gustafsson
2016/0144170 A1 5/2016 Gibson et al.
2016/0205484 A1 7/2016 Nagl et al.
2016/0213936 A1 7/2016 Heerlein et al.
2016/0310737 A1 10/2016 Tourrel et al.
2016/0361537 A1 12/2016 Leigh et al.
2016/0381473 A1 12/2016 Gustafsson
2016/0381474 A1 12/2016 Gustafsson et al.
2017/0050027 A1 2/2017 Andersson et al.
2017/0078808 A1 3/2017 Kennes
2017/0156010 A1 6/2017 Verma et al.
2017/0173334 A1 6/2017 Zimmerling
2017/0239476 A1* 8/2017 Lee ........................... H01F 7/02
2017/0251312 A1 8/2017 Crawford et al.
2017/0347208 A1 11/2017 Jurkiewicz
2018/0028818 A1 2/2018 Anderson et al.

(56) References Cited

U.S. PATENT DOCUMENTS

| | | | | |
|---|---|---|---|---|
| 2018/0056084 | A1 | 3/2018 | Alam | |
| 2018/0110985 | A1 | 4/2018 | Walter | |
| 2018/0110986 | A1* | 4/2018 | Lee | A61N 1/36038 |
| 2018/0133486 | A1* | 5/2018 | Smith | A61N 1/36038 |
| 2018/0146308 | A1 | 5/2018 | Leigh et al. | |
| 2018/0160241 | A1 | 6/2018 | Gustafsson et al. | |
| 2018/0160242 | A1 | 6/2018 | Sriskandarajah | |
| 2018/0185634 | A1 | 7/2018 | Smyth | |
| 2018/0249262 | A1 | 8/2018 | Santek | |
| 2018/0270591 | A1 | 9/2018 | Kennes | |
| 2018/0296826 | A1 | 10/2018 | Lee et al. | |
| 2018/0303602 | A1 | 10/2018 | Leigh | |
| 2018/0304078 | A1 | 10/2018 | Crawford et al. | |
| 2018/0369586 | A1 | 12/2018 | Lee et al. | |
| 2019/0015662 | A1 | 1/2019 | Raje et al. | |
| 2019/0046797 | A1 | 2/2019 | Calixto et al. | |
| 2019/0053908 | A1 | 2/2019 | Cook et al. | |
| 2019/0076649 | A1 | 3/2019 | Lee et al. | |
| 2019/0255316 | A1 | 8/2019 | Lee et al. | |
| 2019/0298417 | A1 | 10/2019 | Barrett et al. | |
| 2020/0114151 | A1 | 4/2020 | Smith et al. | |
| 2020/0230422 | A1 | 7/2020 | Gibson et al. | |
| 2020/0238088 | A1 | 7/2020 | Smith et al. | |
| 2020/0330777 | A1 | 10/2020 | Smith et al. | |
| 2020/0391023 | A1 | 12/2020 | Lee et al. | |
| 2021/0046311 | A1 | 2/2021 | Brehm et al. | |
| 2021/0106815 | A1 | 4/2021 | Smith et al. | |
| 2021/0156934 | A1 | 5/2021 | Smith et al. | |
| 2021/0299456 | A1 | 9/2021 | Smith et al. | |
| 2021/0316136 | A1 | 10/2021 | Smith et al. | |
| 2021/0339021 | A1 | 11/2021 | Brehm et al. | |
| 2022/0273948 | A1 | 9/2022 | Calixto et al. | |
| 2022/0280793 | A1 | 9/2022 | Smith et al. | |
| 2023/0032218 | A1 | 2/2023 | Smith et al. | |
| 2023/0061335 | A1 | 3/2023 | Lee et al. | |
| 2024/0342473 | A1 | 10/2024 | Smith et al. | |
| 2025/0001175 | A1 | 1/2025 | Lee et al. | |
| 2025/0001186 | A1 | 1/2025 | Lee et al. | |
| 2025/0050102 | A1 | 2/2025 | Smith et al. | |

FOREIGN PATENT DOCUMENTS

| | | | | |
|---|---|---|---|---|
| EP | 0241307 | A2 | 10/1987 | |
| EP | 2117489 | B1 | 5/2010 | |
| EP | 2853287 | A1 | 4/2015 | |
| EP | 2560730 | B1 | 11/2016 | |
| EP | 3138605 | A1 | 3/2017 | |
| EP | 2098198 | B1 | 9/2017 | |
| EP | 3964259 | A1 | 3/2022 | |
| RU | 2727227 | C1 | 7/2020 | |
| WO | WO9858990 | A1 | 12/1998 | |
| WO | WO03081976 | A2 | 10/2003 | |
| WO | WO03092326 | A1 | 11/2003 | |
| WO | WO2004004416 | A1 | 1/2004 | |
| WO | WO2004014269 | A1 | 2/2004 | |
| WO | WO2004014270 | A1 | 2/2004 | |
| WO | WO2007024657 | A2 | 3/2007 | |
| WO | WO2009124045 | A1 | 10/2009 | |
| WO | WO2009124174 | A2 | 10/2009 | |
| WO | WO2009149069 | A2 | 12/2009 | |
| WO | WO2010000027 | A1 | 1/2010 | |
| WO | WO2010083554 | A1 | 7/2010 | |
| WO | WO2011011409 | A1 | 1/2011 | |
| WO | WO2011109486 | A2 | 9/2011 | |
| WO | WO2011133747 | A1 | 10/2011 | |
| WO | WO2012010195 | A1 | 1/2012 | |
| WO | WO2013043176 | A1 | 3/2013 | |
| WO | WO2013063355 | A1 | 5/2013 | |
| WO | WO2014011441 | A1 | 1/2014 | |
| WO | WO2014011582 | A2 | 1/2014 | |
| WO | WO2014046662 | A1 | 3/2014 | |
| WO | WO2014164023 | A1 | 10/2014 | |
| WO | WO2015065442 | A1 | 5/2015 | |
| WO | WO2016016821 | A1 | 2/2016 | |
| WO | WO2016190886 | A1 | 12/2016 | |
| WO | WO2016191429 | A1 | 12/2016 | |
| WO | WO2016207856 | A1 | 12/2016 | |
| WO | WO2017027045 | A1 | 2/2017 | |
| WO | WO2017027046 | A1 | 2/2017 | |
| WO | WO2017029615 | A1 | 2/2017 | |
| WO | WO2017034530 | A1 | 3/2017 | |
| WO | WO2017046650 | A1 | 3/2017 | |
| WO | WO2017087004 | A1 | 5/2017 | |
| WO | WO2017105510 | A1 | 6/2017 | |
| WO | WO2017105511 | A1 | 6/2017 | |
| WO | WO2017105604 | A1 | 6/2017 | |
| WO | WO2017172566 | A1 | 10/2017 | |
| WO | WO2018190813 | A1 | 10/2018 | |
| WO | WO2018191314 | A1 | 10/2018 | |
| WO | WO2018199936 | A1 | 11/2018 | |
| WO | WO2018200347 | A1 | 11/2018 | |
| WO | WO2018217187 | A1 | 11/2018 | |
| WO | WO2019027745 | A1 | 2/2019 | |
| WO | WO-2019083540 | A1 * | 5/2019 | A61N 1/36038 |
| WO | WO2019160555 | A1 | 8/2019 | |
| WO | WO2020092185 | A1 | 5/2020 | |
| WO | WO2021201845 | A1 | 10/2021 | |
| WO | WO2023063934 | A1 | 4/2023 | |
| WO | WO2023063983 | A1 | 4/2023 | |
| WO | WO2023113790 | A1 | 6/2023 | |
| WO | WO2024043896 | A1 | 2/2024 | |
| WO | WO2024080978 | A1 | 4/2024 | |

OTHER PUBLICATIONS

Ju Hyun Jeon et al., "Reversing the Polarity of a Cochlear Implant Magnet After Magnetic Resonance Imaging," Auris Nasus Larynx, vol. 39, No. 4, pp. 415-417, Aug. 1, 2012.

Teissl et al., "Magentic Resonance Imaging and Cochlear Implants: Compatibility and Safety Aspects," Journal of Magnetic Resonance Imaging, Society for Magnetic Resonance Imaging, vol. 9, No. 1, pp. 26-38, Jan. 1, 1999.

U.S. Appl. No. 15/568,469, filed Oct. 21, 2017, 20180110985 A1.

U.S. Appl. No. 15/770,207, filed Apr. 22, 2018, U.S. Pat. No. 10,806,936.

U.S. Appl. No. 17/073,322, filed Oct. 17, 2020, 20210170167 A1.

U.S. Appl. No. 16/060,383, filed Jun. 7, 2018, U.S. Pat. No. 10,532,209.

U.S. Appl. No. 15/591,054, filed May 9, 2017, U.S. Pat. No. 9,919,154.

U.S. Appl. No. 16/009,600, filed Jun. 15, 2018, U.S. Pat. No. 10,821,279.

U.S. Appl. No. 16/403,582, filed May 5, 2019, U.S. Pat. No. 10,463,849.

U.S. Appl. No. 17/008,291, filed Aug. 31, 2020, U.S. Pat. No. 11,476,025.

U.S. Appl. No. 17/965,580, filed Oct. 13, 2022, U.S. Pat. No. 11,986,656.

U.S. Appl. No. 16/610,502, filed Nov. 2, 2019, U.S. Pat. No. 11,287,495.

U.S. Appl. No. 15/568,470, filed Oct. 21, 2017, U.S. Pat. No. 10,300,276.

U.S. Appl. No. 16/101,390, filed Aug. 10, 2018, 20190046797 A1.

U.S. Appl. No. 17/680,217, filed Feb. 24, 2022, 20220273948 A1.

U.S. Appl. No. 15/703,808, filed Sep. 13, 2017, U.S. Pat. No. 10,646,712.

U.S. Appl. No. 15/805,025, filed Nov. 6, 2017, U.S. Pat. No. 10,646,718.

U.S. Appl. No. 16/852,457, filed Apr. 18, 2020, 20200238088 A1.

U.S. Appl. No. 16/499,311, filed Sep. 29, 2019, U.S. Pat. No. 11,097,095.

U.S. Appl. No. 17/355,225, filed Jun. 23, 2021, U.S. Pat. No. 11,779,754.

U.S. Appl. No. 16/603,868, filed Oct. 9, 2019, U.S. Pat. No. 11,364,384.

U.S. Appl. No. 17/750,352, filed May 22, 2022, U.S. Pat. No. 11,752,338.

U.S. Appl. No. 16/754,126, filed Apr. 6, 2020, U.S. Pat. No. 11,471,679.

(56) References Cited

OTHER PUBLICATIONS

U.S. Appl. No. 17/964,321, filed Oct. 12, 2022, 20230032218 A1.
U.S. Appl. No. 17,335,161, filed Jun. 1, 2021, U.S. Pat. No. 11,638,823.
U.S. Appl. No. 17/346,343, filed Jun. 14, 2021, 20210299456 A1.
U.S. Appl. No. 18/691,947, filed Mar. 14, 2024, 20240342473 A1.
U.S. Appl. No. 18/718,442, filed Jun. 10, 2024, 20250050102 A1.
U.S. Appl. No. 18/701,147, filed Apr. 12, 2024, 20250001175 A1.
U.S. Appl. No. 17/499,813, filed Oct. 12, 2021, 20230115968 A1.
U.S. Appl. No. 18/701,199, filed Apr. 12, 2024, 20250001186 A1.
U.S. Appl. No. 18/885,649, filed Sep. 14, 2024.

* cited by examiner

COCHLEAR IMPLANTS HAVING MRI-COMPATIBLE MAGNET APPARATUS AND ASSOCIATED SYSTEMS AND METHODS

BACKGROUND

1. Field

The present disclosure relates generally to implantable cochlear stimulation (or "ICS") systems.

2. Description of the Related Art

ICS systems are used to help the profoundly deaf perceive a sensation of sound by directly exciting the intact auditory nerve with controlled impulses of electrical current. Ambient sound pressure waves are picked up by an externally worn microphone and converted to electrical signals. The electrical signals, in turn, are processed by a sound processor, converted to a pulse sequence having varying pulse widths, rates and/or amplitudes, and transmitted to an implanted receiver circuit of the ICS system. The implanted receiver circuit is connected to an implantable electrode array that has been inserted into the cochlea of the inner ear, and electrical stimulation current is applied to varying electrode combinations to create a perception of sound. The electrode array may, alternatively, be directly inserted into the cochlear nerve without residing in the cochlea. A representative ICS system is disclosed in U.S. Pat. No. 5,824,022, which is entitled "Cochlear Stimulation System Employing Behind-The-Ear Sound processor With Remote Control" and incorporated herein by reference in its entirety. Examples of commercially available ICS sound processors include, but are not limited to, the Harmony™ BTE sound processor, the Naida™ CI Q Series sound processor and the Neptune™ body worn sound processor, which are available from Advanced Bionics.

As alluded to above, some ICS systems include an implantable cochlear stimulator (or "cochlear implant"), a sound processor unit (e.g., a body worn processor or behind-the-ear processor), and a microphone that is part of, or is in communication with, the sound processor unit. The cochlear implant communicates with the sound processor unit and, some ICS systems include a headpiece that is in communication with both the sound processor unit and the cochlear implant. The headpiece communicates with the cochlear implant by way of a transmitter (e.g., an antenna) on the headpiece and a receiver (e.g., an antenna) on the implant. Optimum communication is achieved when the transmitter and the receiver are aligned with one another. To that end, the headpiece and the cochlear implant may include respective positioning magnets that are attracted to one another, and that maintain the position of the headpiece transmitter over the implant receiver. The implant magnet may, for example, be located within a pocket in the cochlear implant housing. The skin and subcutaneous tissue that separates the headpiece magnet and implant magnet is sometimes referred to as the "skin flap," which is frequently 3 mm to 11 mm thick.

The present inventors have determined that conventional cochlear implants and stimulation systems are susceptible to improvement. For example, the magnet in some conventional cochlear implant is a disk-shaped axially magnetized magnet that has north and south magnetic dipoles which are aligned in the axial direction of the disk. Such magnets are not compatible with magnetic resonance imaging ("MRI") systems, and may have to be surgically removed from the cochlear the implant prior to the MRI procedure and then surgically replaced thereafter. Other cochlear implants include a diametrically magnetized disk-shaped magnet that is rotatable relative to the remainder of the implant about its central axis, and that has a N-S orientation which is perpendicular to the central axis. The present inventors have determined that diametrically magnetized disk-shaped magnets are less than optimal because a dominant magnetic field, such as the MRI magnetic field, that is misaligned by at least 30° or more from the N-S direction of the magnet may demagnetize the magnet or generate an amount of torque on the magnet that is sufficient to dislodge or reverse the magnet and/or dislocate the associated cochlear implant and/or cause excessive discomfort to the patient.

More recently, cochlear implants with MRI-compatible magnet apparatus have been introduced. The MRI-compatible magnet apparatus have a case defining a central axis, a frame within the case that is rotatable relative to the case about the central axis, and three or more elongate diametrically magnetized magnets that are located in the frame in close proximity to one another and that are rotatable about their respective longitudinal axis relative to the frame. This combination allows the magnets to align with three-dimensional (3D) MRI magnetic fields, regardless of field direction, which results in very low amounts of torque on the magnets. Examples of such MRI-compatible magnet apparatus may be found in U.S. Pat. Nos. 9,919,154, 10,463,849, and 10,532,209. Another proposed magnet apparatus, which includes a single elongate magnet, is described in PCT Pat. Pub. No. 2020/092185 A1.

Although such MRI-compatible magnet apparatus have proven to be a significant advance in the art, the present inventors have determined that they are susceptible to improvement. For example, the field strength of MRI systems continues to increase and the amount of torque associated with placement of a particular MRI-compatible magnet apparatus into a 5 Tesla (5T) MRI magnetic field or a 7 Tesla (7T) MRI magnetic field may be significantly greater than the amount of torque associated with placement of the same MRI-compatible magnet apparatus into a 3 Telsa (3T) MRI magnetic field. The present inventors have also determined that it would be desirable to reduce the amount of magnetic material within a MRI-compatible magnet apparatus, thereby reducing the torque associated with a MRI magnetic field, without a corresponding reduction in the attraction force between the MRI-compatible magnet apparatus and the headpiece magnet, and without a corresponding increase in the size of the headpiece magnet. The present inventors have further determined that it would be desirable to more efficiently employ the magnetic field of the headpiece magnet, thereby further facilitating the use of less magnetic material within the MRI-compatible magnet apparatus.

SUMMARY

A method in accordance with at least one of the present inventions may include positioning a headpiece, including an axially magnetized magnet that defines a N-S direction and an antenna, on a portion of a user's head over an implanted cochlear implant including a magnet apparatus. The magnet apparatus may include a case, a frame within the case and rotatable about the central axis of the case, and only two elongate diametrically magnetized magnets that are located in the frame, that each define a longitudinal axis and a N-S direction, that are rotatable about the longitudinal axis relative to the frame, that are attracted to one another with an attraction force F1, and that are separated from one another by a fixed non-zero distance that is perpendicular to at least one of the longitudinal axes. When the distance between the axially magnetized magnet and the elongate diametrically magnetized magnets is 12 mm, there is a magnetic attraction force F2, which greater than the magnetic attraction force F1, between axially magnetized magnet of the positioned headpiece and the elongate diametrically magnetized magnets.

A system in accordance with at least one of the present inventions may include a head wearable external component, including an axially magnetized external magnet, and a cochlear implant having a cochlear lead, an implant antenna, an implant processor and an implant magnet assembly. The implant magnet assembly may include an implant magnet case defining a central axis, a frame within the implant magnet case and rotatable relative to the implant magnet case about the central axis of the implant magnet case, and only two elongate diametrically magnetized implant magnets that are located in the frame, that each define a longitudinal axis and have an individual magnetic dipole moment, that are rotatable about the longitudinal axis relative to the frame, and that are separated from one another by a fixed non-zero distance that is perpendicular to at least one of the longitudinal axes.

A magnet apparatus in accordance with at least one of the present inventions may include a case, a magnet frame within the case and rotatable about the central axis of the case, and only two elongate diametrically magnetized magnets that are located in the frame, that are separated from one another by a fixed non-zero distance, that each define a longitudinal axis and a N-S direction, that are rotatable about the longitudinal axis relative to the frame, and that are attracted to one another with a magnetic attraction force that is less than 3.0 N.

A magnet apparatus in accordance with at least one of the present inventions may include a case, a magnet frame within the case and rotatable about the central axis of the case, and only two elongate diametrically magnetized magnets that are located in the frame, that are separated from one another by a fixed non-zero distance, that each define a longitudinal axis and a N-S direction, that are rotatable about the longitudinal axis relative to the frame, and that define a total magnet volume that is less than about 20% to about 30% of the internal volume of the case.

A magnet apparatus in accordance with at least one of the present inventions may include a case, a magnet frame within the case and rotatable about the central axis of the case, and only two elongate diametrically magnetized magnets that are located in the frame, that are separated from one another by a fixed distance of about 3.8 mm to about 4.2 mm, that each define a longitudinal axis and a N-S direction, and that are rotatable about the longitudinal axis relative to the frame.

There are a number of advantages associated with such methods and apparatus. By way of example, but not limitation, the use of only two rotatable elongate diametrically magnetized magnets in the magnet apparatus reduces the amount of magnet material within the magnet apparatus, while the spacing between the elongate diametrically magnetized magnets reduces the magnetic attraction between the two magnets. The reduction in the magnetic attraction between the magnets within the magnet apparatus facilitates the use of an axially magnetized headpiece magnet, which is more magnetically efficient that a diametrically magnetized headpiece magnet due to the orientation of the magnetic field, because the magnets within the magnet apparatus will rotate into alignment with the magnetic field of the axially magnetized headpiece magnet. Accordingly, the present methods and apparatus employ less magnetic material within the magnet apparatus, the elongate diametrically magnetized magnets have less attraction force to one another due to the distance between the magnets, and there is less friction between rotating magnets and the inner surface of the case, thereby reducing the torque associated with placement of the magnet apparatus into a MRI magnetic field. As compared to a magnet apparatus with three or more elongate diametrically magnetized magnets, the present two-magnet apparatus also creates less of an MRI artifact (which may facilitate brains scans) and is less costly to manufacture. The present methods and apparatus also do so without reducing the magnetic attraction between the headpiece and the cochlear implant or increasing the size of headpiece magnet.

The above described and many other features of the present inventions will become apparent as the inventions become better understood by reference to the following detailed description when considered in conjunction with the accompanying drawings.

BRIEF DESCRIPTION OF THE DRAWINGS

Detailed descriptions of the exemplary embodiments will be made with reference to the accompanying drawings.

DETAILED DESCRIPTION OF THE EXEMPLARY EMBODIMENTS

Figure 1:
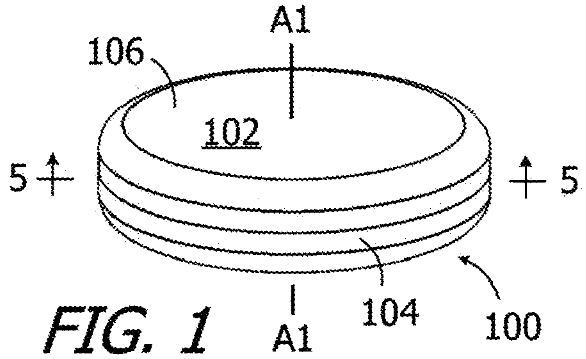
FIG. 1 is a perspective view of an implant magnet apparatus in accordance with one embodiment of a present invention.
Figure 2:
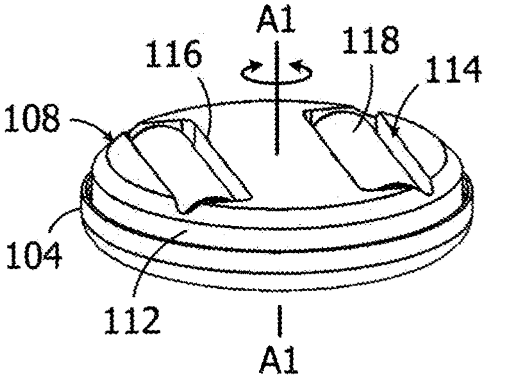
FIG. 2 is a perspective view of a portion of the implant magnet apparatus illustrated in FIG. 1.
Figure 3:
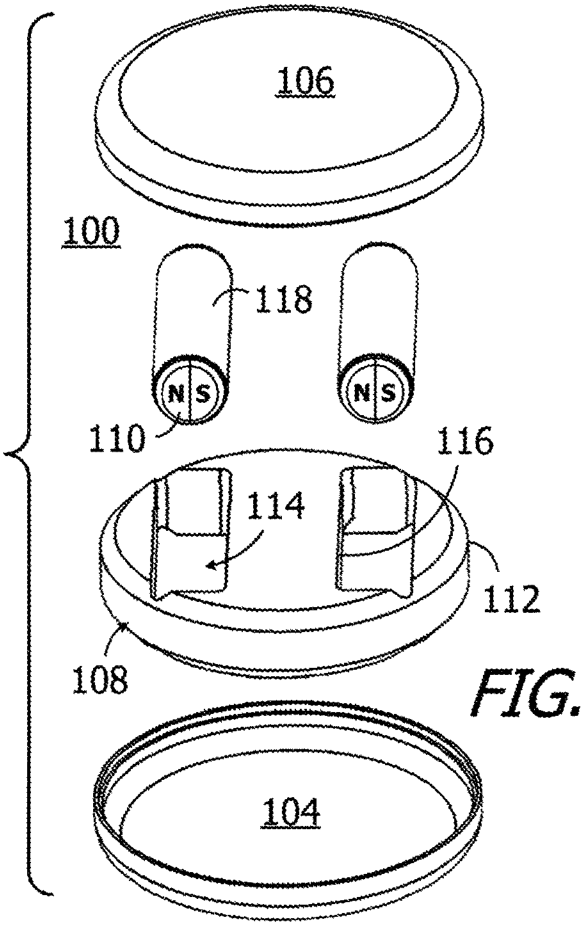
FIG. 3 is an exploded perspective view of the implant magnet apparatus illustrated in FIG. 1.

The following is a detailed description of the best presently known modes of carrying out the inventions. This description is not to be taken in a limiting sense, but is made merely for the purpose of illustrating the general principles of the inventions.

As illustrated for example in FIGS. 1-5A, an exemplary magnet apparatus (or "magnet assembly") 100 includes a case 102, with base 104 and a cover 106, a frame 108 that is rotatable relative to the case, and two elongate diametrically magnetized magnets 110 that are rotatable relative to the frame. The magnet apparatus 100 may, in some instances, be employed in a system 50 (FIG. 6) that includes a cochlear implant 200 with a magnet apparatus 100 (described below with reference to FIG. 16) and an external device such as a headpiece 400 (described below with reference to FIGS. 6 and 17). As is discussed in greater detail below, there are a variety of advantages associated with use of only two magnets that are not in closed proximity to one another. By way of example, but not limitation, the use of only two magnets that are spaced apart results in significantly less magnetic material, as compared to a similarly sized conventional MRI-compatible magnet apparatus, as well as a lower magnetic attraction force between the rotatable magnets which facilitates the use of an axially magnetized headpiece magnet, which is more efficient than the use of a diametrically magnetized headpiece magnet. As a result, a given level of magnetic attraction between the magnet apparatus and the headpiece can be achieved with less magnetic material in the magnet apparatus than would be necessary in a conventional MRI-compatible magnet apparatus and the same amount of magnetic material in the headpiece.

The case 102 in the exemplary magnet apparatus 100 is disk-shaped and defines a central axis A1, which is also the central axis of the frame 108. The frame 108 is rotatable relative to the case 102 about the central axis A1 over 360°. The magnets 110 rotate with the frame 108 about the central axis A1. Each magnet 110 is also rotatable relative to the frame 108 about its own longitudinal axis A2 (also referred to as "axis A2") over 360°. In the exemplary implementation illustrated in FIGS. 1-5A, the longitudinal axes A2 are parallel to one another and are perpendicular to the central axis A1. In other implementations, the magnets may be oriented such that the longitudinal axes thereof are at least substantially perpendicular to the central axis A1. As used herein, an axis that is "at least substantially perpendicular to the central axis" includes axes that are perpendicular to the central axis as well as axes that are slightly non-perpendicular to the central axis (i.e., axes that are offset from perpendicular by up to 5 degrees).

The exemplary case 102 is not limited to any particular configuration, size or shape. In the illustrated implementation, the case 102 is a two-part structure that includes the base 104 and the cover 106 which are secured to one another in such a manner that a hermetic seal is formed between the cover and the base. Suitable techniques for securing the cover 106 to the base 104 include, for example, seam welding with a laser welder. With respect to materials, the case 102 may be formed from biocompatible paramagnetic metals, such as titanium or titanium alloys, and/or biocompatible non-magnetic plastics such as polyether ether ketone (PEEK), low-density polyethylene (LDPE), high-density polyethylene (HDPE), ultra-high-molecular-weight polyethylene (UHMWPE), polytetrafluoroethylene (PTFE) and polyamide. In particular, exemplary metals include commercially pure titanium (e.g., Grade 2) and the titanium alloy Ti-6Al-4V (Grade 5), while exemplary metal thicknesses may range from 0.20 mm to 0.25 mm. With respect to size and shape, the case 102 may have an overall size and shape similar to that of conventional cochlear implant magnets so that the magnet apparatus 100 can be substituted for a conventional magnet in an otherwise conventional cochlear implant. The case 102 may also have an overall size and shape that is larger than that of conventional cochlear implant magnets in other embodiments. In some implementations, the diameter that may range from 9 mm to 17.4 mm and the thickness may range from 1.5 mm to 4.0 mm. The diameter of the case 102 in the illustrated embodiment is about 12.6 mm and the thickness is about 3.1 mm. As used herein in the context of the case 102, the word "about" means±10%.

Figure 4:
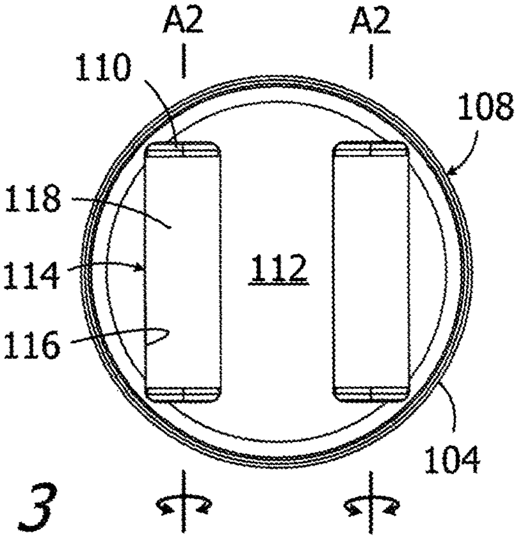
FIG. 4 is a plan view of a portion of the implant magnet apparatus illustrated in FIG. 1.

The exemplary frame 108 includes a disk 112 and only two receptacles 114. A used herein, the phrase "only two" means "two and no more than two." The receptacles 114 extend completely through the disk and that are defined by inner walls 116. Suitable materials for the frame 108, which may be formed by machining, metal injection molding or injection molding, include paramagnetic metals, polymers and plastics such as those discussed above in the context of the case 102. Referring more specifically to FIG. 4, there may be a relatively tight fit between the between the magnets 110 and the receptacles 114. For example, the length of the receptacles 114 may be about 0.05 mm to about 0.20 mm greater than the length of the magnets 110 and the width of the receptacles may be about 0.05 mm to about 0.15 mm greater than the diameter of the magnets 110 in some implementations. As used herein in the context of the frame, the word "about" means±10%.

Figure 5:
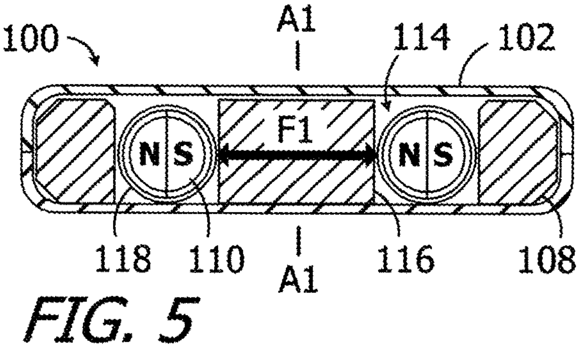
FIG. 5 is a partial section view taken along line 5-5 in FIG. 1.

The magnets 110 in the exemplary magnet apparatus 100 are elongate diametrically magnetized magnets, and there are only two magnets 110 within the case 102. As noted above, the phrase "only two" is used herein to mean "two and no more than two." The exemplary magnets 110 are circular in a cross-section that is perpendicular to the longitudinal axis A2 and, in some instances, may have rounded corners. Suitable materials for the magnets 110 include, but are not limited to, neodymium-boron-iron and samarium-cobalt. The frame 108 maintains the maintains the spacing between the magnets 110. As is discussed in greater detail below, the magnetic attraction force F1 between the two spaced magnets 110, which is a function of the distance between the magnets, is such that the magnets will remain substantially aligned with one another in the N-S direction, as shown in FIG. 5, in the absence of an external magnetic field that is strong enough to rotate the magnets out of alignment. The N-S orientation of each magnet will also be perpendicular to the central axis A1 of the case 102 in the exemplary embodiment. Examples of magnetic fields that are strong enough to rotate the magnets 110 out of N-S alignment with one another are the headpiece magnetic field and the MRI magnetic field that are discussed below with reference to FIGS. 6 and 8.

The magnets 110 may be located within tubes 118 formed from low friction material. Suitable materials for the tubes 118 include polymers, such as silicone, PEEK and other plastics, PTFE, and PEEK-PTFE blends, and paramagnet metals. The magnets 110 may be secured to the tubes 118 such that the each tube rotates with the associated magnet about its axis A2, or the magnets may be free to rotate relative to the tubes. The magnet/tube combination is also more mechanically robust than a magnet alone. The magnets 110 may, in place of the tubes 118, be coated with the lubricious materials discussed below.

Figure 5A:
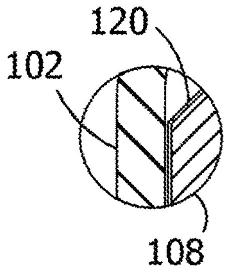
FIG. 5A is an enlarged portion of the section view illustrated in FIG. 5.

Friction may be further reduced by coating the inner surfaces of the case 102 and/or the surfaces of the frame 108 with a lubricious layer. The lubricious layer may be in the form of a specific finish of the surface that reduces friction, as compared to an unfinished surface, or may be a coating of a lubricious material such as diamond-like carbon (DLC), titanium nitride (TiN), PTFE, polyethylene glycol (PEG), Parylene, fluorinated ethylene propylene (FEP) and electroless nickel sold under the tradenames Nedox® and Nedox PF™. The DLC coating, for example, may be only 0.5 to 5 microns thick. In those instances where the base 104 and a cover 106 are formed by stamping, the finishing process may occur prior to stamping. Micro-balls, biocompatible oils and lubricating powders may also be added to the interior of the case to reduce friction. In the illustrated implementation, the surfaces of the frame 108 may be coated with a lubricious layer 120 (e.g., DLC), while the inner surfaces of the case 102 do not include a lubricious layer, as shown in FIG. 5A. The lubricious layer 120 reduces friction between the case 102 and frame 108.

Figure 6:
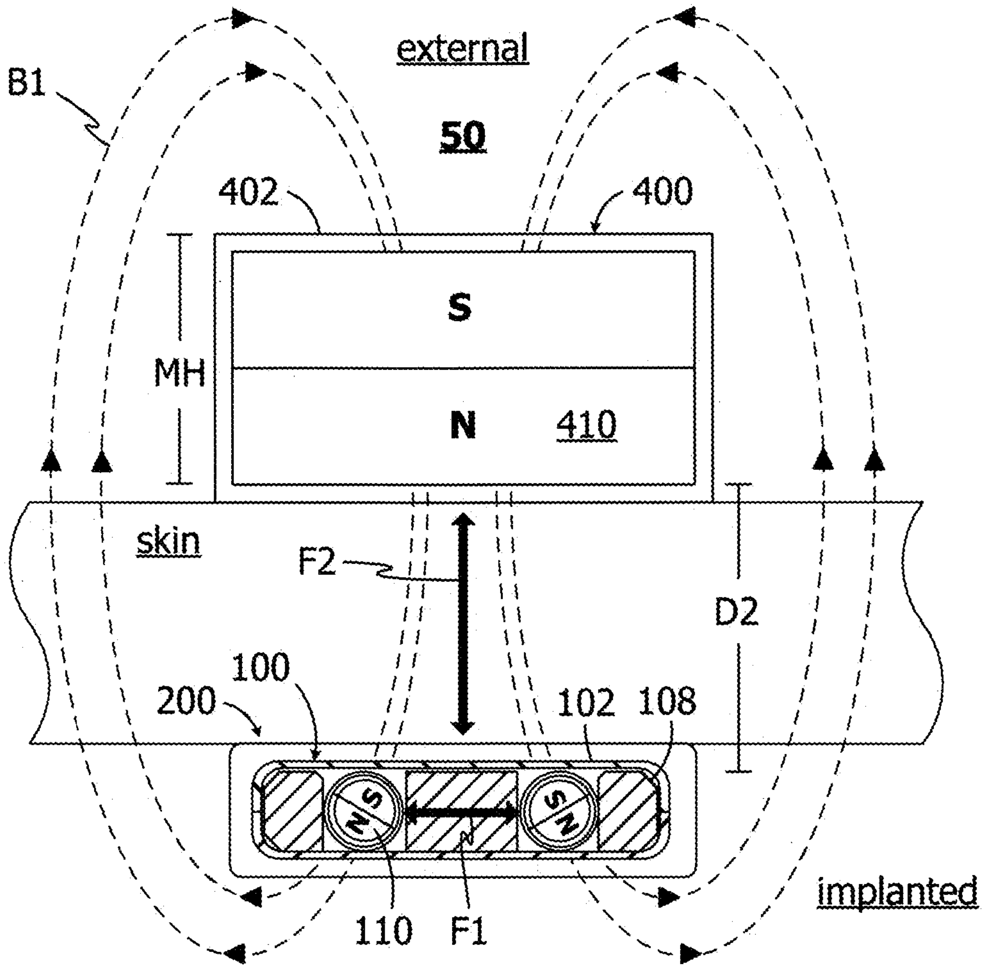
FIG. 6 is a partial section view of a system including a headpiece and an implant with the magnet apparatus illustrated in FIG. 1.

Referring to FIG. 6, the exemplary magnet apparatus 100 may part of an implanted cochlear implant 200 with a housing 202 (described in detail below with reference to FIG. 16) that is employed in conjunction with an external device such as a headpiece 400 (described in detail below with reference to FIG. 17) in a system 50. The exemplary headpiece 400 includes, among other things, a housing 402 and an axially magnetized disk-shaped positioning magnet (or "external magnet") 410. The N-S direction of the external magnet 410 is at least substantially perpendicular (i.e., is perpendicular ±5%) to the implant recipient's skin. The respective configurations of the magnet apparatus 100 and the headpiece 400 are such that when the implanted magnets 110 are exposed to the magnetic field B1 of the axially magnetized external magnet 410, the magnetic attraction force F2 between the external magnet 410 and the implanted magnets 110 is greater than magnetic attraction force F1 between the two spaced apart elongate diametrically magnetized magnets 110. The magnetic attraction force F2 may be, for example, at least 10% greater than the magnetic attraction force F1, or may be, for example, at least 20% greater than the magnetic attraction force F1. As a result, the magnets 110 advantageously rotate out of alignment with one another, and into alignment with the magnetic field B1 of the axially magnetized external magnet 410. Put another way, the individual magnetic dipole moments of the elongate diametrically magnetized implant magnets 110 are oriented substantially in the direction of the axially magnetized external magnet 410 during attractive transcutaneous magnetic interaction with the axially magnetized external magnet 410. The axially magnetized magnet 410 will also align with the center of the magnet apparatus 100, thereby aligning the headpiece antenna with the implant antenna. The magnets 110 will return to the N-S-S aligned state illustrated in FIG. 5 when the headpiece 400 and the associated magnetic field B1 is removed.

Another aspect of the exemplary magnet apparatus 100 is the impact resistance associated with the locations of the elongate diametrically magnetized magnets 110. When the magnet apparatus 100 is subjected to an impact force (e.g., when the user bumps his/her head), the central portion of the case 102 will deflect inwardly. Advantageously, the magnets 110 are offset from the central axis A1 of the case 102 by the distance D1 (FIG. 7), which reduces the likelihood of damage to the magnets as compared to a similar magnet apparatus where at least some of the magnets are located at or near the central axis A1.

Figure 7:
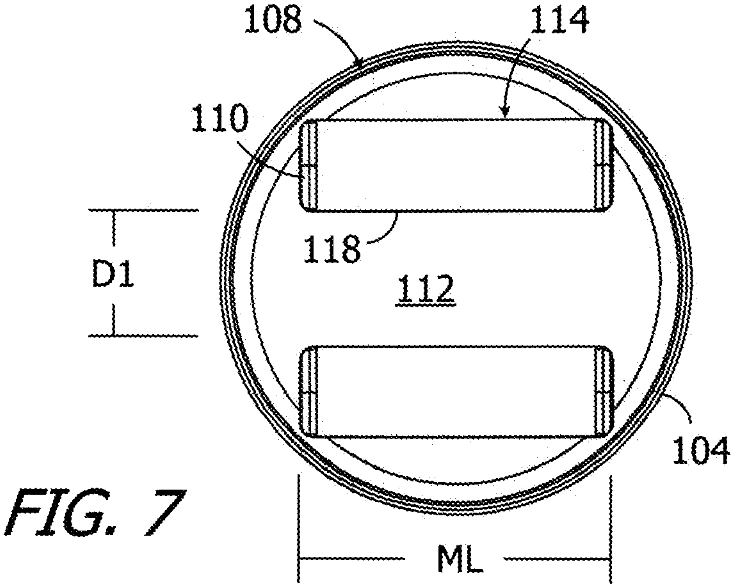
FIG. 7 is a plan view of a portion of the implant magnet apparatus illustrated in FIG. 1.

Referring also to FIG. 7, in the illustrated embodiment, the case 102 is about 12.6 mm in diameter, about 3.1 mm thick and has an internal volume of about 290 mm$^3$. The diametrically magnetized magnets 110 may be N52 neodymium magnets or N55 neodymium magnets, while the axially magnetized headpiece magnet 410 may be a N55 neodymium magnet. The exemplary diametrically magnetized magnets 110 may each have a length ML of about 8.3 mm, a diameter of about 2.3 mm, and a volume of 69 mm$^3$. As used herein in the context of the magnets 110 and 410, the word "about" means±5%. The combined volume of the magnets 110 may be less than about 20% to about 30% of the internal volume of the case 102 and, in the illustrated implementation, is less than about 24% of the internal volume of the case 102. The magnets 110 may be separated by a distance D1 that is about 3.8 mm to about 4.2 mm, as are the frame receptacles 114. The distance D1 is perpendicular to at least one of the longitudinal axes A2, and is perpendicular to both of the longitudinal axes A2 in the illustrated embodiment. The axially magnetized magnet 410 may have a height MH of about 7.6 mm and a diameter of about 11.45 mm. So configured, the magnetic attraction force F1 between the magnets 110 is about 0.24 N, while the magnetic attraction force F2 between the magnets 110 and the magnet 410 is about 0.29 N when there is a distance D2 of 12 mm between the magnets 110 and the magnet 410. As used herein in the context of the magnetic attraction force, the word "about" means±10%, so long as the magnetic attraction force F2 is greater than the magnetic attraction force F1. In at least some embodiments, the magnetic attraction force F2 is at least 10% greater than the magnetic attraction force F1.

It should be noted here that although the diametrically magnetized magnets 110 are identical to one another, are parallel to one another, and are equidistant from the central axis A1 of the case 102 in the illustrated embodiment, the present magnet apparatus are no so limited. By way of example, but not limitation, the diametrically magnetized magnets 110 may have different lengths and/or may have different diameters and/or may be formed from materials having the same or different strength. Alternatively, or in addition, the diametrically magnetized magnets 110 may be non-parallel, and be different distances from the central axis A1 of the case 102. The configurations of the receptacles 114 would be adjusted to accommodate that of the magnets 110.

Figure 8:
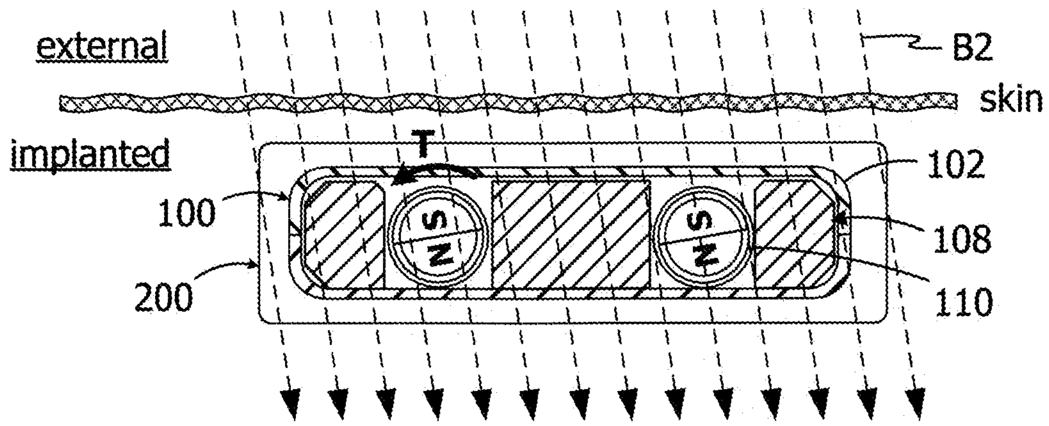
FIG. 8 is a partial section view similar to FIG. 6 with the implant in an MRI magnetic field.
Figure 9:
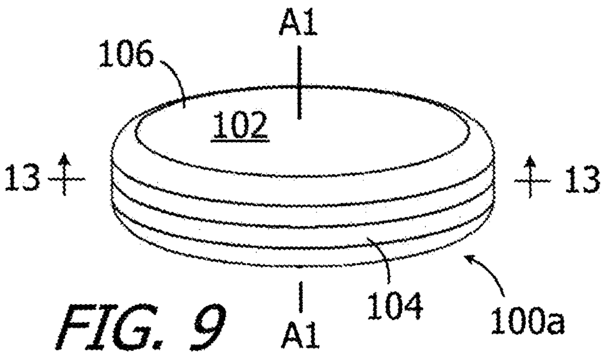
FIG. 9 is a perspective view of an implant magnet apparatus in accordance with one embodiment of a present invention.
Figure 10:
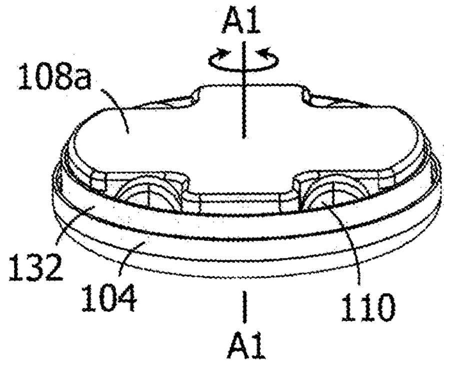
FIG. 10 is a perspective view of a portion of the implant magnet apparatus illustrated in FIG. 9.
Figure 11:
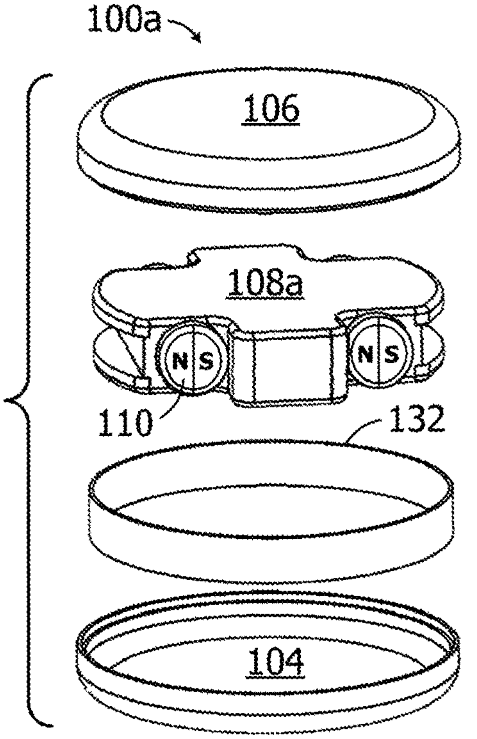
FIG. 11 is an exploded perspective view of the implant magnet apparatus illustrated in FIG. 9.
Figure 12:
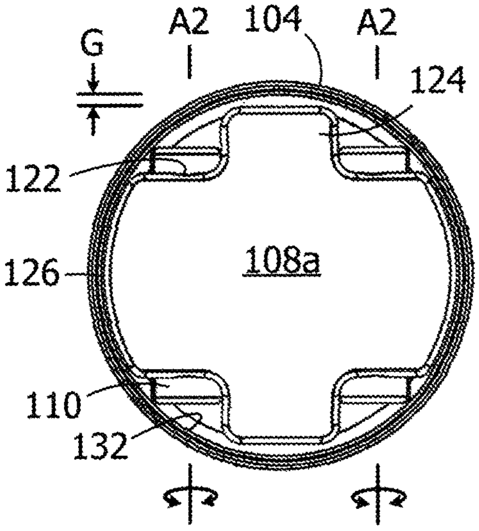
FIG. 12 is a plan view of a portion of the implant magnet apparatus illustrated in FIG. 9.
Figure 13:
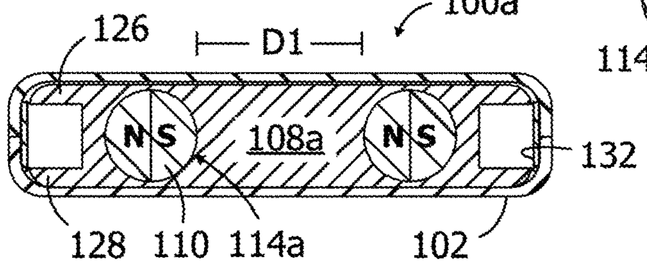
FIG. 13 is a section view taken along line 13-13 in FIG. 9.
Figure 14:
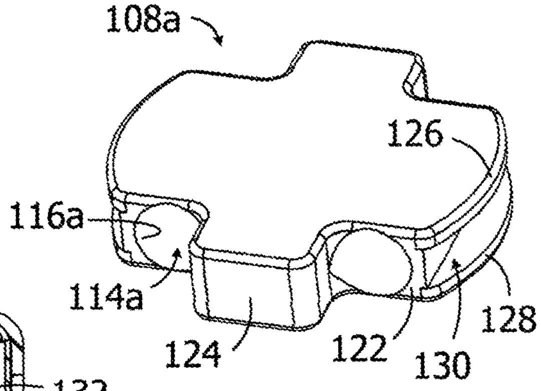
FIG. 14 is a perspective view of a portion of the implant magnet apparatus illustrated in FIG. 9.

Turning to FIG. 8, when exposed to a dominant MRI magnetic field B2, the torque T on the magnets 110 will rotate the magnets about their axis A2 (FIG. 4), thereby aligning the magnetic fields of the magnets 110 with the MRI magnetic field B2. The frame 108 will also rotate about axis A1 as necessary to align the magnetic fields of the magnets 110 with the MRI magnetic field B2. When the magnet apparatus 100 is removed from the MRI magnetic field B2, the magnetic attraction between the magnets 110 will cause the magnets to rotate about axis A2 back to the orientation illustrated in FIG. 5, where they are substantially aligned with one another in the N-S direction.

Another exemplary magnet apparatus is generally represented by reference numeral 100*a* in FIGS. 9-14. Magnet apparatus 100*a* is substantially similar to magnet apparatus 100 and similar elements are represented by similar reference numerals. For example, the magnet apparatus 100*a* includes a case 102, with a base 104 and a cover 106, and only two magnets 110. Here, however, the frame 108*a* includes a pair of relatively short rectangular portions 122 that are separated by a relatively long rectangular portion 124. A pair of receptacles 114*a* defined by tubular walls 116*a* that are located within relatively short rectangular portions 122. The elongate diametrically magnetized magnets 110 are located within the receptacles 114*a* and are rotatable relative to the frame 108*a*. The spacing between the magnets 110 is maintained by the frame 108*a*. The distance between the magnets 110 and the headpiece magnet 410 will also be the same, or substantially the same. As such, the magnets 110 function in the manner described above, both with respect to one another and with respect to the headpiece magnet 410. In the illustrated implementation, upper and lower curved flanges 126 and 128 extend radially outwardly from each of the relatively short rectangular portions 122. The curvature of the free ends of the flanges 126 and 128 corresponds to the curvature of the surface within the case 102 that is in contact with the frame 108*a*.

Figure 15:
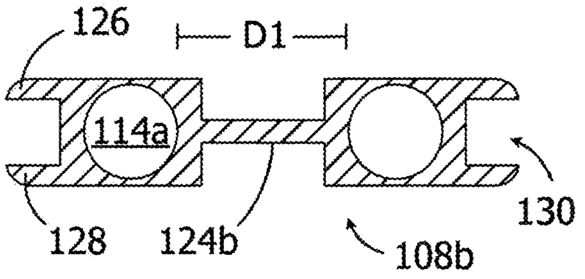
FIG. 15 is a section view of a frame in accordance with one embodiment of a present invention.

Suitable materials for the frame 108*a* include those discussed above with reference to the case 102 and frame 108. By way of example, but not limitation, the frame 108*a* may be formed from a DLC coated metal material. In the illustrated implementation, the frame 108*a* is formed from molded PEEK and an open region 130 defined between the upper and lower curved flanges 126 and 128. The lack of molded material in the open region 130 prevents distortion of the molded frame 108*a* as the frame cools during the manufacturing process. Material may be removed from other portions of a molded frame for the same reason. To that end, the exemplary fame 108*b* illustrated in FIG. 15 includes relatively long rectangular portion 124*b* that is thinner than the relatively long portion 124.

The PEEK (or other molded material) may be protected from the heat associated with the welding of the case cover 106 to the base 104 through the use of a titanium ring 132 that is positioned against the inner surface of the case 102. The titanium ring 132 may be omitted when a metal frame 108*a* is employed.

Figure 16:
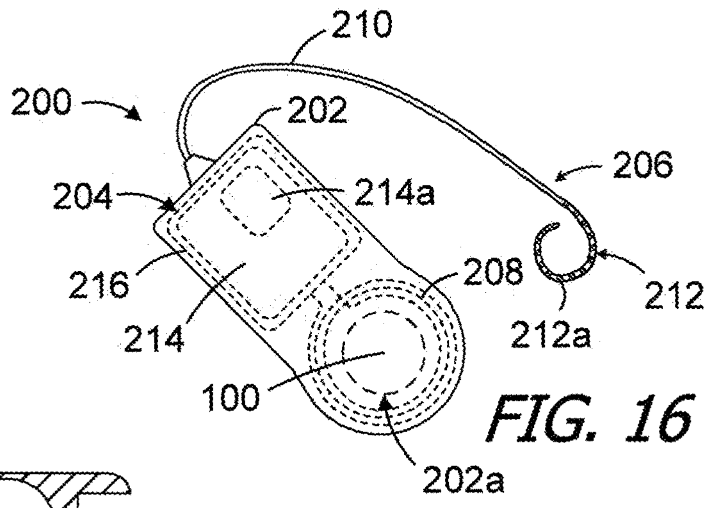
FIG. 16 is a top view of a cochlear implant in accordance with one embodiment of a present invention.

One example of a cochlear implant (or "implantable cochlear stimulator") including the present magnet apparatus 100 (or 100*a*) is the cochlear implant 200 illustrated in FIG. 16. The cochlear implant 200 includes a flexible housing 202 formed from a silicone elastomer or other suitable material, a processor assembly 204, a cochlear lead 206, and an antenna 208 that may be used to receive data and power by way of an external antenna that is associated with, for example, a sound processor unit. The cochlear lead 206 may include a flexible body 210, an electrode array 212 at one end of the flexible body, and a plurality of wires (not shown) that extend through the flexible body from the electrodes 212*a* (e.g., platinum electrodes) in the array 212 to the other end of the flexible body. The magnet apparatus 100 is located within a region encircled by the antenna 208 (e.g., within an internal pocket 202*a* defined by the housing 202) and insures that an external antenna (discussed below) will be properly positioned relative to the antenna 208. The exemplary processor assembly 204, which is connected to the electrode array 212 and antenna 208, includes a printed circuit board 214 with a stimulation processor 214*a* that is located within a hermetically sealed case 216. The stimulation processor 214*a* converts the stimulation data into stimulation signals that stimulate the electrodes 212*a* of the electrode array 212.

Figure 17:
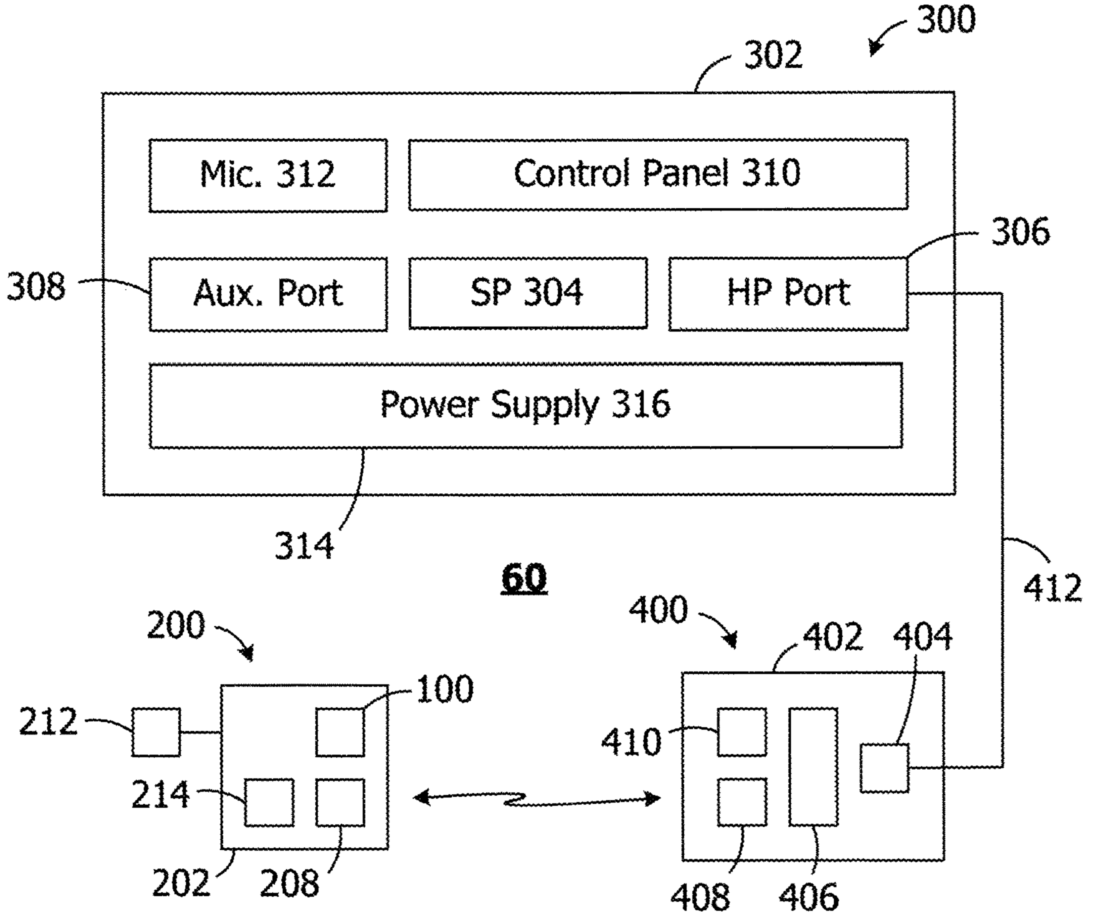
FIG. 17 is a block diagram of a cochlear implant system in accordance with one embodiment of a present invention.
Figure 18:
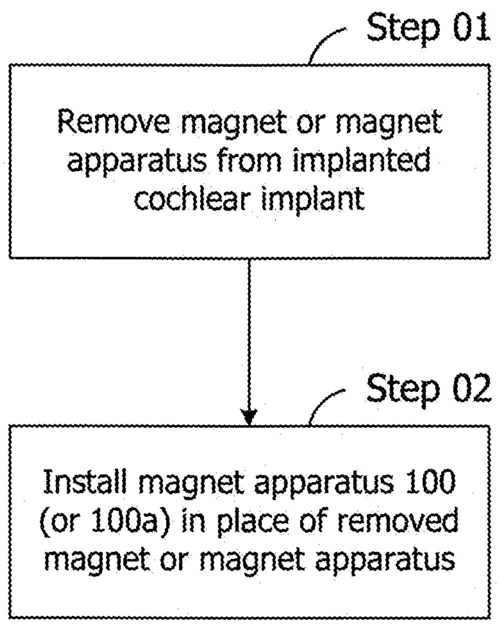
FIG. 18 is a flow chart showing a method in accordance with one embodiment of a present invention.

Turning to FIG. 17, the exemplary cochlear implant system 60 includes the cochlear implant 200, a sound processor, such as the illustrated body worn sound processor 300 or a behind-the-ear sound processor, and a headpiece 400.

The exemplary body worn sound processor 300 in the exemplary ICS system 60 includes a housing 302 in which and/or on which various components are supported. Such components may include, but are not limited to, sound processor circuitry 304, a headpiece port 306, an auxiliary device port 308 for an auxiliary device such as a mobile phone or a music player, a control panel 310, one or more microphones 312, and a power supply receptacle 314 for a removable battery or other removable power supply 316 (e.g., rechargeable and disposable batteries or other electrochemical cells). The sound processor circuitry 304 converts electrical signals from the microphone 312 into stimulation data. The exemplary headpiece 400 includes a housing 402 and various components, e.g., a RF connector 404, a microphone 406, an antenna (or other transmitter) 408 and an axially magnetized disk-shaped positioning magnet 410, that are carried by the housing. The headpiece 400 may be connected to the sound processor headpiece port 306 by a cable 412. The external positioning magnet 410 is attracted to the magnet apparatus 100 of the cochlear stimulator 200 (see FIG. 6), thereby aligning the antenna 408 with the antenna 208. The stimulation data and, in many instances power, is supplied to the headpiece 400. The headpiece 400 transcutaneously transmits the stimulation data, and in many instances power, to the cochlear implant 200 by way of a wireless link between the antennae. The stimulation processor 214*a* converts the stimulation data into stimulation signals that stimulate the electrodes 212*a* of the electrode array 212.

In at least some implementations, the cable 412 will be configured for forward telemetry and power signals at 49 MHz and back telemetry signals at 10.7 MHz. It should be noted that, in other implementations, communication between a sound processor and a headpiece and/or auxiliary device may be accomplished through wireless communication techniques. Additionally, given the presence of the microphone(s) 312 on the sound processor 300, the microphone 406 may be also be omitted in some instances.

The functionality of the sound processor 300 and headpiece 400 may also be combined into a single head wearable sound processor that includes all of the external components (e.g., the battery, microphone, sound processor, antenna coil and magnet). Examples of head wearable sound processors are illustrated and described in U.S. Pat. Nos. 8,811,643 and 8,983,102, which are incorporated herein by reference in their entirety. Headpieces and head wearable sound processors are collectively referred to herein as "head wearable external components."

The present inventions are applicable to systems that include cochlear implants which have already been implanted into the recipient. For example, a similarly sized magnet, or a magnet apparatus with a similarly sized case, may be removed in situ from an implanted cochlear implant (Step 01). In some instances, the magnet or magnet apparatus may be removed from a pocket in the cochlear implant housing. The exemplary magnet apparatus 100 (or 100*a*) described herein may be installed in place of the removed magnet or magnet apparatus (Step 02). In some instances, the magnet apparatus 100 (or 100*a*) may be inserted into the same pocket in the cochlear implant housing from which magnet or magnet apparatus was removed. Suitable removal and installation tools and techniques are illustrated and described in U.S. Pat. No. 10,124,167, which is incorporated herein by reference in its entirety. The headpiece magnet in the associated system may, if necessary, be removed from the headpiece or other head wearable external component and replaced with an axially magnetized magnet.

Although the inventions disclosed herein have been described in terms of the preferred embodiments above, numerous modifications and/or additions to the above-described preferred embodiments would be readily apparent to one skilled in the art. The inventions include any combination of the elements from the various species and embodiments disclosed in the specification that are not already described. It is intended that the scope of the present inventions extend to all such modifications and/or additions and that the scope of the present inventions is limited solely by the claims set forth below.

We claim:

1. A method, comprising:

positioning a head wearable external component, including an axially magnetized magnet that defines a N-S direction and an antenna, on a portion of a user's head over an implanted cochlear implant including a magnet apparatus;

wherein the magnet apparatus includes a case that defines a central axis, a frame within the case and rotatable about the central axis of the case, and only two elongate diametrically magnetized magnets that are located in the frame, that each define a longitudinal axis and a N-S direction, that are rotatable about the longitudinal axis relative to the frame, and that are separated from one another by a fixed non-zero distance D1 that is perpendicular to at least one of the longitudinal axes;

wherein the elongate diametrically magnetized magnets are formed from magnetic material and define a configuration, and the axially magnetized magnet is formed from magnetic material and defines a configuration;

wherein the material and configuration of the elongate diametrically magnetized magnets are such that the elongate diametrically magnetized magnets are attracted to one another with an attraction force F1 and, absent a dominant magnetic force, will align with one another in the N-S direction;

wherein there is a distance D2 between the axially magnetized magnet of the positioned head wearable external component and the elongate diametrically magnetized magnets; and wherein the materials and configurations of the axially magnetized magnet and the elongate diametrically magnetized magnets are such that, when the distance D2 is 12 mm, there is a magnetic attraction force F2, which is greater than the magnetic attraction force F1, between axially magnetized magnet of the positioned head wearable external component and the elongate diametrically magnetized magnets of the implanted cochlear implant.

2. A method as claimed in claim 1, wherein the magnetic attraction force F2 is at least about 10% greater than the magnetic attraction force F1 when the distance D2 is 12 mm.

3. A method as claimed in claim 1, wherein the axially magnetized magnet comprises an N55 magnet having a diameter of about 11.45 mm and a length of about 7.6 mm; and the elongate diametrically magnetized magnets comprise N52 magnets each having a diameter of about 2.3 mm and a length of about 8.3 mm.

4. A method as claimed in claim 3, wherein the fixed non-zero distance D1 is about 3.8 mm to about 4.2 mm.

5. A method as claimed in claim 4, wherein the frame includes two receptacles;

one of the elongate diametrically magnetized magnets is located in each of the receptacles; and the receptacles are separated by the non-zero distance D1.

6. A method as claimed in claim 1, wherein the axially magnetized magnet generates a magnetic field;

portions of the magnetic field pass through the elongate diametrically magnetized magnets; and the materials and configurations of the axially magnetized magnet and the elongate diametrically magnetized magnets are such that, when the distance D2 is 12 mm, the respective N-S directions of the elongate diametrically magnetized magnets will align with the portions of the magnetic field that pass through the elongate diametrically magnetized magnets.

7. A method as claimed in claim 1, wherein the N-S direction of the axially magnetized magnet is at least substantially perpendicular to the portion of a user's head.

8. A method as claimed in claim 1, wherein the case defines an internal volume; and the elongate diametrically magnetized magnets define a total magnet volume that is less than about 20% to about 30% of the internal volume of the case.

9. A system, comprising:

a cochlear implant having a cochlear lead including a plurality of electrodes, an implant antenna, an implant processor operably connected to the implant antenna and to the cochlear lead, and an implant magnet assembly, adjacent to the implant antenna, including an implant magnet case defining a central axis, a frame within the implant magnet case and rotatable relative to the implant magnet case about the central axis of the implant magnet case, and only two elongate diametrically magnetized implant magnets that are located in the frame, that each define a longitudinal axis and have an individual magnetic dipole moment, that are rotatable about the longitudinal axis relative to the frame, and that are separated from one another by a fixed non-zero distance D1 that is perpendicular to at least one of the longitudinal axes; and a head wearable external component including an axially magnetized external magnet and an external antenna adjacent to the axially magnetized external magnet;

wherein the individual magnetic dipole moments of the elongate diametrically magnetized implant magnets are oriented substantially in the direction of the axially magnetized external magnet during attractive transcutaneous magnetic interaction with the axially magnetized external magnet.

10. A system as claimed in claim 9, wherein the elongate diametrically magnetized implant magnets are formed from magnetic material and define a configuration, and the axially magnetized external magnet is formed from magnetic material and defines a configuration;

the materials and configurations of the elongate diametrically magnetized implant magnets are such that they are attracted to one another with an attraction force F1 and, absent a dominant magnetic force, the magnetic dipole moments will align with one another; and the material and configuration of the axially magnetized external magnet and the elongate diametrically magnetized implant magnets are such that, when there is a distance D2 of 12 mm between the axially magnetized external magnet and the elongate diametrically magnetized implant magnets, there is a magnetic attraction force F2, which greater than the magnetic attraction force F1, between axially magnetized external magnet of the positioned head wearable external component and the elongate diametrically magnetized implant magnets.

11. A system as claimed in claim 10, wherein the magnetic attraction force F2 is at least about 10% greater than the magnetic attraction force F1 when the distance D2 is 12 mm.

12. A system as claimed in claim 9, wherein the implant magnet case defines an internal volume; and the elongate diametrically magnetized implant magnets define a total magnet volume that is less than about 20% to about 30% of the internal volume of the implant magnet case.

13. A system as claimed in claim 9, wherein the fixed non-zero distance D1 is about 3.8 mm to about 4.2 mm.

14. A system as claimed in claim 9, wherein the frame includes two receptacles;

one of the elongate diametrically magnetized implant magnets is located in each of the receptacles; and the receptacles are separated by the non-zero distance D1.

15. A system as claimed in claim 9, wherein the axially magnetized external magnet comprises an N55 magnet having a diameter of about 11.45 mm and a length of about 7.6 mm; and the elongate diametrically magnetized implant magnets comprise N52 magnets each having a diameter of about 2.3 mm and a length of about 8.3 mm.

* * * * *